United States Patent [19]

Galantay et al.

[11] 3,952,035

[45] Apr. 20, 1976

[54] ORGANIC COMPOUNDS

[75] Inventors: Eugène Ervin Galantay, Liestal; Heribert Wagner, Pfeffingen, both of Switzerland

[73] Assignee: Sandoz Ltd., (Sandoz AG), Basel, Switzerland

[22] Filed: Apr. 19, 1974

[21] Appl. No.: 462,292

[30] Foreign Application Priority Data

Apr. 25, 1973  Switzerland.......................... 5884/73

[52] U.S. Cl............................ 260/413; 260/410.9 R; 424/318; 260/DIG. 44
[51] Int. Cl.².................... C11C 1/00; C01B 25/16
[58] Field of Search............. 260/413, 405.5, 526 N, 260/DIG. 44; 424/318

[56] References Cited

UNITED STATES PATENTS

| 3,033,884 | 5/1962 | Osbond............................. 260/413 |
| 3,299,111 | 1/1967 | Adams et al....................... 260/413 |
| 3,824,262 | 7/1974 | Heslinga et al.................... 260/413 |
| 3,862,972 | 1/1975 | Heslinga et al.................... 260/413 |

FOREIGN PATENTS OR APPLICATIONS 32,921  12/1962  Finland.............................. 260/413

*Primary Examiner*—Patrick P. Garvin
*Assistant Examiner*—P. E. Konopka
*Attorney, Agent, or Firm*—Gerald D. Sharkin; Robert S. Honor

[57] ABSTRACT

The invention concerns novel unsaturated fatty acids useful as inhibitors of prostoglandin synthetase.

12 Claims, No Drawings

ORGANIC COMPOUNDS

The present invention relates to new unsaturated fatty acids, and derivatives thereof.

In accordance with the invention there are provided compounds of formula I,

wherein
$n$ is an integer from 0 to 4,
$p$ is the integer 3 or 4, with the proviso that when $p = 3$, $n$ must be 2 to 4, and when $p = 4$, $n$ must be 0 or 1, and
Z is one of the radicals of formula IIa,

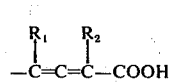

wherein $R_1$ and $R_2$ are, independently, hydrogen or lower alkyl, of formula IIb,

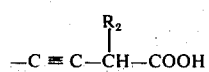

wherein $R_2$ is hydrogen or lower alkyl, or of formula IIc,

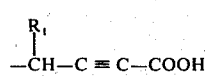

wherein $R_1$ is hydrogen and lower alkyl. Lower alkyl preferably signifies alkyl groups of 1 to 4 carbon atoms.

Further, in accordance with the invention a compound of formula I may be obtained by a process comprising
a. saponifying a compound of formula V,

wherein
$n$ is an integer from 0 to 4,
$p$ is the integer 3 or 4, with the proviso that when $p = 3$, $n$ must be 2 to 4, and when $p = 4$, $n$ must be 0 or 1, and
Y is one of the radicals of formula VIa,

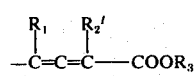

wherein
$R_1$ is hydrogen or lower alkyl,
$R_2'$ is lower alkyl, and
$R_3$ is lower alkyl,
or of formula VIb,

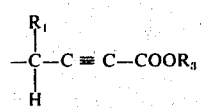

wherein
$R_1$ is hydrogen or lower alkyl, and $R_3$ is lower alkyl,
to obtain a compound of formula Ia

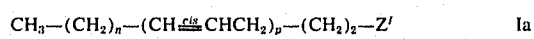

wherein $n$ and $p$ are as defined above and $Z^I$ is one of the radicals of formula II aa,

wherein
$R_1$ is as defined above, and
$R_2'$ is lower alkyl,
of formula IIba,

wherein $R_2'$ is lower alkyl, or of formula IIc as defined above, or
b. isomerizing a compound of formula Ib,

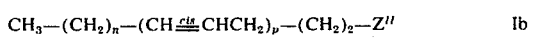

wherein $n$ and $p$ are as defined above and $Z^{II}$ is the radical of formula IIab,

wherein $R_1'$ is hydrogen, and $R_2$ is as defined above, or of formula IIc as defined above to obtain a compound of formula Ic

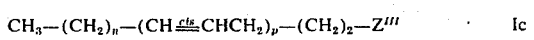

wherein $n$ and $p$ are as defined above, and $Z^{III}$ is one of the radicals of formula IIac

wherein
$R_1$ is as defined above, and
$R_2''$ is hydrogen or
of formula IIb as defined above.

Process variant (a) may be effected as follows:
The reaction may be carried out under conventional conditions for the saponification of acetylenic or allenic esters. Alkaline conditions may be used, for example caustic soda. Preferably the caustic soda is present in a dilute, e.g. 1N, aqueous solution. Room temperature is a suitable reaction temperature.

It will be appreciated that partial alkaliinduced isomerization may occur during the reaction, especially when Y is a radical of formula IIa wherein $R_1$ is hydrogen to form a radical of formula IIba.

Process variant (b) may be effected as follows:
The reaction may be carried out under conventional conditions for isomerization of allenic and propargyl acids. Strongly basic conditions are convenient. Preferably sodium amide is used in an inert solvent such as liquid ammonia. A suitable temperature is from −80° to −30°C. Alternatively caustic soda in dimethyl sulphoxide (produced in situ by the addition of the theoretical amount of water to a $NaCH_2.SO.CH_3$ solution in dimethylsulphoxide) or potassium tert-butylate in tert-butanol or dimethylformamide may be used, for example at 20° to 70°C.

Compounds of formula V may be produced by condensing a compound of formula III,

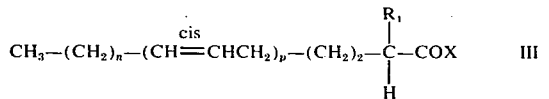

wherein
$n$ is an integer from 0 to 4,
$p$ is the integer 3 or 4, with the proviso that when $p = 3$, $n$ must be 2 to 4, and when $p = 4$, $n$ must be 0 or 1,
$R_1$ is hydrogen or lower alkyl, and
X is chlorine, bromine or iodine,
with a compound of formula IV,

wherein
$R_2$ is hydrogen or lower alkyl, and
$R_3$ is lower alkyl,

The reaction may be carried out under conventional witting conditions. Suitable inert solvents are aromatic hydrocarbon solvents, e.g. benzene or toluene, or ether solvents such as 1,2-dimethoxyethane or tetrahydrofuran. The reaction is preferably carried out at about room temperature.

Insofar as the production of any of the starting materials has not been particularly described, these compounds are known or may be produced and purified, e.g. under an inert gas atmosphere where necessary, in an accordance with known processes or in a manner analogous to the processes described herein or to known processes.

Free acid forms of compounds of formula I may be converted into salt forms in conventional manner and vice versa.

Metal salts include salts with sodium, potassium, calcium, magnesium or aluminum, and salts of amines include those with ammonia, trishydroxymethylaminomethane, triethylamine, 2-dimethylaminoethanol, 2-diethylaminoethanol, lysine or arginine.

It will be appreciated that compounds of formula I wherein Z is the radical IIa, or a radical IIb or IIc wherein $R_1$ or $R_2$ is lower alkyl, may exist in individual optical isomeric forms. Such compounds generally may be obtained from appropriate optically active starting materials, e.g. a compound of formula III, or by separation of a racemic compound I mixture into individual optical isomeric forms by conventional techniques, e.g. using an optically active base.

It will be appreciated that the reactions mentioned above are conveniently carried out in an inert gas atmosphere, e.g. of nitrogen.

In the following non-limitative Examples all temperatures are indicated in degrees Centigrade and are uncorrected.

EXAMPLE 1 d,1-2-methyl-2,3,8cis,11cis,14ciseicosapentaenoic acid and
d,1-2-methyleicosa-8cis,11cis,14cistrien-3-ynoic acid a. d,1-2-methyl-2,3,8cis,11cis,14cis-eicosapentaenoic acid ethyl ester 1.02 g of γ-linolenic acid chloride are added to a solution of 2.59 g of triphenylphosphine-[1-ethoxycarbonyl-ethylide] in 8.3 cc of absolute tetrahydrofuran, and stirring is effected at 22° for 24 hours in an atmosphere of nitrogen. 50 cc of pentane are then added, filtration is effected and the filtrate is concentrated. The resulting title compound is purified by chromatography on a silica gel column (with benzene as eluant). It exhibits a characteristical NMR and IR spectrum for the structure:

NMR ($CDCl_3$) e.g.: 3 proton doublet (J = 1.5 cps) at δ 1.88 ppm: methyl group in 2 position. 4 proton quasi-triplet at δ 2.83 ppm: methylene groups in positions 10 and 13.

IR ($CH_2Cl_2$): allene band at 1958 $cm^{-1}$.

b. d,1-2-methyl-2,3,8cis,11cis,14cis-eicosapentaenoic acid 31 g of the ethyl ester obtained in section (a) above are dissolved in a mixture of 270 cc of ethanol and 90 cc of 1 N caustic soda solution, and the solution is allowed to stand at 22° for 24 hours in an atmosphere of nitrogen. The main portion of the ethanol is then distilled off in a vacuum, 300 cc of water are added, the solution is first washed with pentane and then acidified with 90 cc of 1 N hydrochloric acid. The crude d,1-2-methyl-2,3,8cis,11cis,14cis-eicosapentaenoic acid is subsequently obtained by extraction with hexane. Further purification or separation of d,1-2-methyleicosa-8cis,11cis,14cis-trien-3-ynoic acid is effected by chromatography on a silica gel column in an atmosphere of nitrogen.

The desired allenic acid is eluted with benzene/acetone (5 %) and obtained as viscous oil. $R_f$ = 0.525 (benzene/acetone 2:1, silica gel plate).

NMR spectrum: $\delta\delta_{CDCl_3}$: 7 protons at 5.35 ppm (m); 4 at 2.74 (t); 6 at 2.12 (m); 3 at 1.88 (d, J = 3 cps); 8 at 1.30 (m) and 3 at 0.90 (t).

IR spectrum: 1958 and 1680 $cm^{-1}$.

The production of a pharmacologically acceptable salt is effected by dissolving the title compound in 5 cc of methanol and adding a solution of 0.952 g of trishydroxymethylaminomethane in 30 cc of methanol. The resulting solution of the salt is concentrated by evaporation and crystallized with ethyl acetate.

c. d,1-2-methyleicosa-8cis,11cis,14cis-trien-3-ynoic acid

Further elution of the column indicated in Example 1 b) with benzene/acetone (50 %) yields the acetylenic acid with the above structure. $R_f$ = 0.502 (benzene/acetone 2:1, silica gel plate).

NMR spectrum: $\delta\delta_{CDCl_3}$: 6 protons at 5.35 ppm (m); 1 at 3.40 (m); 4 at 2.74 (t); 6 at 2.12 (m); 3 at 1.51 (d, J = 7 cps); 8 at 1.30 (m) and 3 at 0.90 (t).

IR spectrum: 1740 $cm^{-1}$.

The racemic acids of formula I, obtained in Example 1, may be separated into the optical antipodes in accordance with known methods by reaction with a suitable optically active base, whereby the d- or 1-2-methyl-2,3,8cis,11cis,14cis-eicosapentaenoic acid, as well as the d- or 1-2-methyleicosa-8cis,11cis,14cis-trien-3-ynoic acid are obtained.

The following may, for example, be produced in a manner analogous to that described in Example 1:

d,1-2,4-dimethyl-2,3,8cis,11cis,14cis-eicosapentaenoic acid;

d,1-2-ethyl-2,3,8cis,11cis,14cis,17cis-eicosahexaenoic acid, as well as d,1-2-ethyleicosa-8cis,11cis,17-cis-trien-3-ynoic acid.

EXAMPLE 2

8cis,11cis,14cis-eicosatrien-2-ynoic acid and d,1-2,3,8cis,11cis,14cis-eicosapentaenoic acid a. 8cis,11cis,14cis-eicosatrien-2-oic acid ethyl ester 1.00 g of γ-linolenic acid chloride is added to a solution of 2.30 g of triphenylphosphine-[ethoxycarbonylmethylide] in 20 cc of benzene. After 2 hours the separated precipitate is filtered off and the filtrate is concentrated in a vacuum. The residue is pyrolyzed in a high vacuum at a temperature of 220°–240° (with simultaneous distillation of the pyrolysis product). The distillate is taken up in hexane, is filtered and concentrated to obtain the oily title compound.

b. 8cis,11cis,14cis-eicosatrien-2-ynoic acid

8cis,11cis,14cis-eicosatrien-2-ynoic acid ethyl ester is converted into the title compound or a salt form thereof in a manner analogous to that described in Example 1 (b).

c. d,1-2,3,8cis,11cis,14cis-eicosapentaenoic acid 1.6 g of 8cis,11cis,14cis-eicosatrien-2-ynoic acid in 10 cc of ether are added at −35° to a solution of 2.0 g of sodium amide in 30 cc of liquid ammonia. After standing for 15 hours at −35°, the ammonia is removed by evaporation and the mixture is poured into an excess of ice-cold 0.1 N hydrochloric acid. The desired allenic acid is obtained by extraction (hexane) and chromatographic purification (silica gel, elution with benzene-/acetone 95:5).

During this isomerization 8cis,11cis,14cis-eicosatrien-3-ynoic acid is slowly formed as additional product within a reaction of equilibrium, and this acid may be obtained during the course of the chromatographic purification of the allenic acid by a further elution step.

The eicosapentaenoic acid obtained as racemate in Example 2 may be separated into the d- or 1-antipodes in accordance with known methods by reaction with a suitable optically active base.

The following may, for example, also be produced in a manner analogous to that described in Example 2:

analogous 2 b: d,1-4-methyleicosa-8cis,11cis,14cis-trien-2-ynoic acid and d,1-4-ethyleicosa-8cis,11cis,14-cis-trien-2-ynoic acid;

analogous 2 c: d,1-4-methyl-2,3,8cis,11cis,14cis-eicosapentaenoic acid, and d,1-4-ethyleicosa-2,3,8cis,11cis,14cis-eicosapentaenoic acid.

The compounds of formula I have not been described in the literature.

The compounds of formula I are useful because they possess pharmacological acitivity in animals. In particular, the compounds of formula I are useful as inhibitors of prostoglandin synthetase as indicated in standard tests for example by an inhibition of effects induced by natural prostoglandins, e.g. $PGF_2 \alpha$, in smooth muscles of the stomach and colon of rats on administration of from 1 mg of 15 mg/kg animal body weight of the compounds and have little or no effect at lower doses when no prostoglandin is present in accordance with the principles of Gilmore N., Vane R. I., Wyllie I. H. Nature 218, 1135–40 (1968), by an inhibition of the effect of arachidonic acid on the guinea pig ileum on administration of from 1 to 10 μg/ml of the compounds and have little or no effect when arachidonic acid is absent in accordance with the principles of Bisset G. W., Haldar J., Lewin J. E. (Memoirs of the Society for Endocrinology No. 14) and Endogenous substances affecting the myometrium. Edited by V. R. Pickles and R. J. Fitzpatrick (Cambridge University Press 1966. p 185–198 ), by an inhibition of the constrictions of the isolated rat uterus on administration of from 5 to 30 mg/liter of the compounds after stimulation with $PGE_1$, $PGF_2 \alpha$, acetylcholine or oxytocin, and by an inhibition of spontaneous motility in the rat uterus in situ on infusion of 20 to 80 μg/minute of the compounds over e.g. 14 minutes in accordance with the principles of Ruegg M., Jaques R., Exper. 28, 1525 (1972). Jaques R., Helv. Physiol. Acta 17, 255 (1959) and Jaques R., Helv. Physiol. Acta 23, 156 (1965).

Because of their utility as inhibitors of prostoglandin synthetase the compounds are useful in the inhibition of inflammations, treatment of migraine, spasmolysis of the gastrointestinal tract in the case of diarrhea, inhibition of uterus contractions, e.g. during menstruation, prevention of bronchospasms induced by endogenous $PGF_2 \alpha$, prevention of depressing effects in the central nervous system, induced by endogenous prostoglandins, prevention of the depressing effect or endogenous synthesized prostoglandins on the sympathetic nervous system activities such as lipolysis, inotropic effect on the heart in the case of stress conditions, e.g. surgical operations, coldness and sports, and inhibition of platelet aggregation.

For the above mentioned uses the dosage will, of course, vary depending on the compound employed, mode of administration and therapy desired. However, in general, satisfactory results are obtained when administered at a daily dosage of from 0.1 mg to about 15 mg per kg animal body weight, conveniently given in divided doses 2 to 4 times a day or in sustained release form. For the larger mammal, the total daily dosage is in the range from about 10 to about 1000 mg, and dosage forms suitable for oral administration comprise from about 2 mg to about 500 mg of the compounds admixed with a solid or liquid pharmaceutical carrier or diluent.

The compounds of formula I may be administered in pharmaceutically acceptable salt form. Such salt forms exhibit the same order of activity as the free forms and are readily prepared in conventional manner. Representative salt forms include the salt forms mentioned above. A pharmaceutical composition may comprise a compound of formula I, in free form or in pharmaceutically acceptable salt form, in association with a pharmaceutical carrier or diluent. Such compositions conveniently contain more than 1 % by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

What is claimed is:

1. A compound of the formula,
$$CH_3-(CH_2)_n-(CH \stackrel{cis}{=} CHCH_2)_p-(CH_2)_2-Z \quad I$$
wherein
  $n$ is an integer from 0 to 4,
  $p$ is the integer 3 or 4, with the proviso that when $p = 3$, $n$ must be 2 to 4, and when $p = 4$, $n$ must be 0 or 1, and
  Z is one of the radicals of formula IIa,

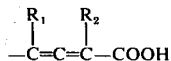     IIa wherein $R_1$ and $R_2$ are, independently, hydrogen or lower alkyl, of formula IIb,

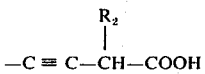     IIb wherein $R_2$ is hydrogen or lower alkyl, or of formula IIc,

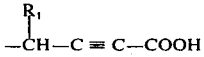     IIc wherein $R_1$ is hydrogen and lower alkyl, or a pharmaceutically acceptable salt thereof.

2. The compound of claim 1 which is 2-methyl-2,3,8cis,11cis,14cis-eicosapentaenoic acid.

3. The compound of claim 1 which is 2-methyleicosa-8cis,11cis,14cis-trien-3-ynoic acid.

4. The compound of claim 1 which is 2,4-dimethyl-2,3,8cis,11cis,14cis-eicosapentaenoic acid.

5. The compound of claim 1 which is 2-ethyl-2,3,8cis,11cis,14cis,17cis-eicosahexaenoic acid.

6. The compound of claim 1 which is 2-ethyleicosa-8cis,11cis,17cis-trien-3-ynoic acid.

7. The compound of claim 1 which is 8cis-11cis,14-cis-eicosatrien-2-ynoic-acid.

8. The compound of claim 1 which is 2,3,8cis,11cis,14cis-eicosapentaenoic acid.

9. The compound of claim 1 which is 4-ethyleicosa-8cis,11cis,14cis-trien-2-ynoic acid.

10. The compound of claim 1 which is 4-ethyleicosa-8cis,11cis,14cis-trien-2-ynoic acid.

11. The compound of claim 1 which is 4-methyl-2,3,8cis,11cis,14cis-eicosapentaenoic acid.

12. The compound of claim 1 which is 4-ethyleicosa-2,3,8cis,11cis,14cis-eicosapentaenoic acid.

* * * * *